US012729231B2

(12) United States Patent
Han et al.

(10) Patent No.: US 12,729,231 B2
(45) Date of Patent: Sep. 8, 2026

(54) FUSION PROTEIN HAVING TRIPLE ACTIVITY AND USE THEREOF

(71) Applicant: SHANGHAI MINWEI BIOTECHNOLOGY CO., LTD, Shanghai (CN)

(72) Inventors: Weiyue Han, Shanghai (CN); Guitao Zhang, Shanghai (CN); Dixiang Luo, Shanghai (CN); Wenxin Song, Shanghai (CN); Shaodong Zhong, Shanghai (CN); Dan Liu, Shanghai (CN); Jiangtao Peng, Shanghai (CN)

(73) Assignee: SHANGHAI MINWEI BIOTECHNOLOGY CO., LTD, Shanghai (CN)

( * ) Notice: Subject to any disclaimer, the term of this patent is extended or adjusted under 35 U.S.C. 154(b) by 0 days.

(21) Appl. No.: 19/555,320

(22) Filed: Mar. 3, 2026

(65) Prior Publication Data

US 2026/0176323 A1 Jun. 25, 2026

Related U.S. Application Data

(63) Continuation of application No. 19/109,867, filed as application No. PCT/CN2023/072953 on Jan. 18, 2023.

(51) Int. Cl.

| | |
|---|---|
| ***C07K 14/605*** | (2006.01) |
| ***A61K 38/00*** | (2006.01) |
| ***A61P 3/04*** | (2006.01) |
| ***A61P 3/10*** | (2006.01) |
| ***C07K 14/50*** | (2006.01) |
| ***C07K 14/575*** | (2006.01) |
| ***C07K 14/645*** | (2006.01) |

(52) U.S. Cl.

CPC .............. *C07K 14/605* (2013.01); *A61P 3/04* (2018.01); *A61P 3/10* (2018.01); *C07K 14/50* (2013.01); *C07K 14/575* (2013.01); *C07K 14/645* (2013.01); *A61K 38/00* (2013.01); *C07K 2319/30* (2013.01)

(58) Field of Classification Search

CPC .... C07K 14/605; C07K 14/50; C07K 14/645; C07K 2319/30; A61P 3/04; A61P 3/10; A61K 38/00

See application file for complete search history.

(56) References Cited

U.S. PATENT DOCUMENTS

| | | | | |
|---|---|---|---|---|
| 8,883,981 | B2 * | 11/2014 | Shitara | C07K 16/2887 530/387.3 |
| 2013/0085098 | A1 * | 4/2013 | Dickinson | A61P 3/06 514/6.9 |
| 2015/0141327 | A1 * | 5/2015 | Darling | C07K 14/50 514/4.8 |
| 2021/0070829 | A1 | 3/2021 | Huang | |
| 2021/0196794 | A1 * | 7/2021 | Chen | A61K 38/1825 |
| 2022/0064244 | A1 * | 3/2022 | Chen | A61P 1/16 |
| 2022/0127322 | A1 | 4/2022 | Chen et al. | |
| 2022/0340635 | A1 | 10/2022 | Huang | |
| 2025/0223331 | A1 * | 7/2025 | Jiang | A61K 47/6811 |

FOREIGN PATENT DOCUMENTS

| | | | |
|---|---|---|---|
| CN | 110087671 | A | 8/2019 |
| CN | 113278060 | A | 8/2021 |
| CN | 115109166 | A | 9/2022 |
| CN | 115515641 | A | 12/2022 |
| CN | 116284441 | B | 12/2023 |
| CN | 118344461 | A | 7/2024 |
| JP | 2020509761 | A | 4/2020 |
| JP | 2022518850 | A | 3/2022 |
| RU | 2741345 | C2 | 1/2021 |
| WO | WO-2009149171 | A2 | 12/2009 |
| WO | WO-2011020319 | A1 | 2/2011 |
| WO | WO-2013033452 | A2 | 3/2013 |
| WO | WO-2016190697 | A1 | 12/2016 |
| WO | WO-2018166461 | A1 | 9/2018 |
| WO | WO-2020177712 | A1 | 9/2020 |
| WO | WO-2022079639 | A1 | 4/2022 |
| WO | WO-2022177744 | A1 | 8/2022 |
| WO | WO-2022241287 | A2 | 11/2022 |
| WO | WO-2022257479 | A1 | 12/2022 |
| WO | WO-2022268029 | A1 | 12/2022 |
| WO | WO-2023030444 | A1 | 3/2023 |
| WO | WO-2024152259 | A1 | 7/2024 |
| WO | WO-2024152419 | A1 | 7/2024 |
| WO | WO-2024260414 | A1 | 12/2024 |

OTHER PUBLICATIONS

Parekh (mAbs (2012) 4(3): 310-318) (Year: 2012).*

Kumar et al., "Therapeutic targets, novel drugs, and delivery systems for diabetes-associated NAFLD and liver fibrosis," Advanced Drug Delivery Reviews, (Sep. 2021); 176:113888, 35 pages. doi: 10.1016/j.addr.2021.113888. Epub Jul. 24, 2021. PMID: 34314787.

Li et al., "A novel GLP-1/GIP/Gcg triagonist reduces cognitive deficits and pathology in the 3xTg mouse model of Alzheimer's disease," Hippocampus, (May 2018); 28(5):358-372. doi: 10.1002/hipo.22837. Epub Mar. 5, 2018. PMID: 29473979.

Pan et al., "A novel GLP-1 and FGF21 dual agonist has therapeutic potential for diabetes and non-alcoholic steatohepatitis," EBioMedicine, (Jan. 2021); 63:103202, 14 pages. doi: 10.1016/j.ebiom.2020.103202. Epub Jan. 7, 2021. PMID: 33421947.

(Continued)

*Primary Examiner* — Julie Wu
*Assistant Examiner* — Elizabeth A Shupe
(74) *Attorney, Agent, or Firm* — COOLEY LLP; Andrew T. Wilkins; Megan E. Coyle

(57) ABSTRACT

A fusion protein having a triple activity and a use thereof are provided. More specifically, a fusion protein has a triple biological activity of glucagon-like peptide-1 (GLP-1), glucose-dependent insulinotropic polypeptide (GIP), and epidermal growth factor 21 (FGF21). It can be used for treating type 2 diabetes (T2D), obesity, and other diseases related to glucose and lipid metabolic abnormalities.

26 Claims, 1 Drawing Sheet

Specification includes a Sequence Listing.

(56) References Cited

OTHER PUBLICATIONS

PCT Application No. PCT/CN2023/072953, International Preliminary Report on Patentability mailed Jul. 31, 2025, Applicant: Shanghai Minwei Biotechnology Co., Ltd, 13 pages.
PCT Application No. PCT/CN2023/072953, International Search Report and Written Opinion mailed Sep. 2, 2023, Applicant: Shanghai Minwei Biotechnology Co., Ltd, 19 pages.
U.S. Appl. No. 19/109,867, filed Mar. 7, 2025; Inventor Han, Weiyue et al.
Wang, "Designing a dual GLP-1R/GIPR agonist from tirzepatide: comparing residues between tirzepatide, GLP-1, and GIP," Drug Design, Development and Therapy, (May 25, 2022); 16:1547-1559. doi: 10.2147/DDDT.S358989. PMID: 35651477.
Weng et al., "Glyco-engineered long-acting FGF21 variant with optimal pharmaceutical and pharmacokinetic properties to enable weekly to twice-monthly subcutaneous dosing," Scientific Reports, (Mar. 9, 2018); 8(1):4241, 15 pages. doi: 10.1038/s41598-018-22456-w. PMID: 29523796.
Zhang et al., "Research progress of GLP-1/GIP double receptor agonists in the treatment of type 2 diabetes mellitus," Zhejiang Medical Journal, (Oct. 30, 2022); 44(20):2227-2231.

* cited by examiner

FUSION PROTEIN HAVING TRIPLE ACTIVITY AND USE THEREOF

RELATED APPLICATIONS

This application is a continuation of U.S. application Ser. No. 19/109,867, filed Mar. 7, 2025, which is a U.S. National Phase application of PCT/CN2023/072953, filed Jan. 18, 2023, the contents of each of which are incorporated herein by reference in their entireties.

INCORPORATION OF SEQUENCE LISTING

This application contains a sequence listing submitted in Computer Readable Form (CRF). The CRF file contains the sequence listing entitled "SDRA_001_01US_SequenceListing.xml", which was created on Mar. 3, 2026, and is 30,877 bytes in size. The information in the sequence listing is incorporated herein by reference in its entirety.

TECHNICAL FIELD

The present invention relates to the field of biomedicine, and specifically relates to a fusion protein having triple activity and use thereof.

BACKGROUND

Diabetes and obesity are diseases caused by abnormal glucose and lipid metabolism, which are associated with a variety of other diseases, including cardiovascular disease (CVD), peripheral arterial disease, microvascular complications, and osteoarthritis. Therefore, the development of new therapies and therapeutic drugs for obesity, diabetes and their complications are of great significance to improve human health.

Fibroblast growth factor 21 (FGF21) is a member of fibroblast growth factors (FGFs) family with 182 amino acids. FGF21 can promote the absorption of glucose by adipocytes, enhance insulin sensitivity, and does not pose a potential tumor risk due to its lack of mitogenic activity. At present, no FGF21 long-acting protein product is available on the market. LY2405319 from Lilly, PF-05231023 from Pfizer and BMS 986036 from Bristol Squibb are now in clinical trials. However, they can not meet the clinical requirements in the treatment of type 2 diabetes, and they are not as effective as GLP-1 drugs in reducing weight and blood lipids. Therefore, it can be seen that FGF21 alone cannot meet clinical needs.

Recently, research has reported that the combination of GLP-1 and FGF21 has a synergistic effect on blood glucose control and weight loss. Prior arts have disclosed that the combination of GLP-1 and FGF21 can synergistically reduce blood glucose and body weight, etc.

At present, although the GLP-1/GIP dual active analog (Tirzepatide), FGF21 analog and GLP-1/FGF21 fusion protein are all used to treat diabetes and lose weight, their effects are still unsatisfactory, and there is no report on GLP-1/GIP/FGF21 triple active protein in this field.

Therefore, there is an urgent need in this field to develop a fusion protein with GLP-1/GIP/FGF21 triple activity that can be effectively used to treat diabetes and lose weight.

SUMMARY OF THE INVENTION

The purpose of the present invention is to provide a fusion protein with triple activity and use thereof.

Specifically, the present invention provides a fusion protein having a triple bioactivity of glucagon-like peptide-1 (GLP-1), glucose-dependent insulinotropic polypeptide (GIP), and epidermal growth factor 21 (FGF21) for the treatment of type 2 diabetes (T2D), obesity, and other diseases related with glucose and lipid metabolic abnormality.

In the first aspect of the present invention, it provides a fusion protein which has a structure as shown in formula I or formula II from N-terminus to C-terminus:

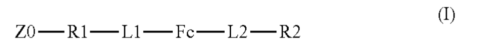

(I)

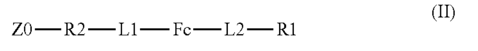

(II)

wherein,

Z0 is absent, or selected from: a signal peptide, a tag sequence, or a combination thereof;

R1 is a mutant protein element of GLP-1 and GIP;

L1 is absent or a linker peptide;

Fc is an Fc element;

L2 is absent or a linker peptide;

R2 is a FGF21 element;

"-" is a bond, wherein, the mutant protein element of GLP-1 and GIP comprises a GLP-1 and GIP mutant protein, wherein the amino acid sequence of the mutant protein is a polypeptide sequence based on the amino acid sequence shown in SEQ ID NO: 20 with amino acid residues at positions 1, 2, 13, 19, 21, 23, 24 selected from the group consisting of:

His or Tyr at position 1,

Gly or Ser at position 2,

Tyr or Leu at position 13,

Ala or Gln at position 19,

Ala or Asp at position 21,

Val or Ile at position 23, and

Ala or Gln or Glu at position 24; and wherein the mutant protein has activity of binding and activating both a class B G protein-coupled receptor GLP-1R and a human glucose-dependent insulinotropic polypeptide (GIP) receptor.

In another preferred embodiment, the amino acid sequence of the mutant protein is shown in any one of SEQ ID NOs: 8-19.

In another preferred embodiment, the FGF21 element comprises FGF21 wild-type or a mutant thereof.

In another preferred embodiment, the amino acid sequence of the FGF21 wild-type is shown in SEQ ID NO: 1.

In another preferred embodiment, the amino acid sequence of the FGF21 mutant is a polypeptide sequence based on the amino acid sequence shown in SEQ ID NO: 1 with amino acid residues at positions 19, 98, 171, and/or 173 selected from the group consisting of: R19V, L98R, P171N, Q173T.

In another preferred embodiment, the amino acid sequence of the FGF21 mutant is identical or substantially identical to the sequence shown in SEQ ID NO: 1, except for the mutations (such as amino acid residues at positions 19, 98, 171, and/or 173).

In another preferred embodiment, the substantially identical means that at most 10 amino acids (preferably 1-8, more preferably 1-10, more preferably 1-5) are different, wherein the differences comprise substitution, deletion, or addition of amino acids, and the mutant still retains the activity of fibroblast growth factor 21 (FGF21).

In another preferred embodiment, the fusion protein may be modified or unmodified.

In another preferred embodiment, the amino acid sequence of the FGF21 mutant is shown in SEQ ID NO: 2.

In another preferred embodiment, the amino acid sequence of $R^2$ is shown in SEQ ID NO: 1 or 2.

In another preferred embodiment, the fusion protein has both activity of binding and activating a class B G protein-coupled receptor GLP-1R and a human glucose-dependent insulinotropic polypeptide (GIP) receptor, and activity of fibroblast growth factor 21 (FGF21).

In another preferred embodiment, the Fc element is an Fc fragment of immunoglobulin IgG, wherein the IgG is selected from the group consisting of: IgG1, IgG2, and IgG4, preferably IgG4.

In another preferred embodiment, the sequence of the Fc element is shown in SEQ ID NO: 21.

In another preferred embodiment, the Fc fragment comprises the hinge region, CH2 and CH3 domains of IgG4.

In another preferred embodiment, L1 and/or L2 are flexible linkers.

In another preferred embodiment, the amino acid sequence of L1 and/or L2 is (G4S) n or (G4S) nA or a variant thereof, wherein n is a positive integer (for example, 1, 2, 3, 4, 5 or 6), preferably, n=3. In another preferred embodiment, the variant of (G4S) n comprises: a variant of the $(G4S)_nA$ linker sequence obtained by substituting an amino acid in the sequence with one having similar or close properties, for example, substituting one or more S into T respectively; or inserting 1-3 amino acids into the sequence.

In another preferred embodiment, L1 and L2 are the same or different.

In another preferred embodiment, Lls are each independently $(G4S)_nA$, wherein n is a positive integer selected from 2 to 5 (for example, 1, 2, 3, 4, 5, or 6), preferably n is 3.

In another preferred embodiment, L2s are each independently (G4S) n, wherein n is a positive integer selected from 2 to 5 (for example, 1, 2, 3, 4, 5, or 6), preferably n is 3.

In another preferred embodiment, the sequence of L1 is shown in SEQ ID NO: 22.

In another preferred embodiment, the sequence of L2 is shown in SEQ ID NO: 23.

In another preferred embodiment, the fusion protein has an amino acid sequence selected from the group consisting of:

(a) a sequence shown in any one of SEQ ID NOs: 4-7;

(b) an amino acid sequence having at least 80%, preferably at least 85% or 90%, more preferably at least 95%, more preferably at least 98%, and more preferably at least 99% homology to a sequence shown in any one of SEQ ID NOs: 4-7;

wherein the fusion protein has both activity of binding and activating a class B G protein-coupled receptor GLP-1R and a human glucose-dependent insulinotropic polypeptide (GIP) receptor, and activity of fibroblast growth factor 21 (FGF21).

In the second aspect of the present invention, it provides an isolated polynucleotide encoding the fusion protein according to the first aspect of the present invention.

In the third aspect of the present invention, it provides a vector comprising the polynucleotide according to the second aspect of the present invention.

In another preferred embodiment, the vector is selected from the group consisting of: DNA, RNA, plasmid, lentiviral vector, adenoviral vector, retroviral vector, transposon, and a combination thereof.

In the fourth aspect of the present invention, it provides a host cell which comprises the vector according to the third aspect of the present invention, or has the polynucleotide according to the second aspect of the present invention exogenously integrated into its genome.

In the fifth aspect of the present invention, it provides a method for preparing the fusion protein according to the first aspect of the present invention, which comprises the following steps:

(i) culturing the host cell according to the fourth aspect of the present invention under a suitable condition, thereby obtaining a mixture comprising the fusion protein according to the first aspect of the present invention; and (ii) purifying and/or separating the mixture obtained in step (i), thereby obtaining the fusion protein according to the first aspect of the present invention.

In the sixth aspect of the present invention, it provides a pharmaceutical composition comprising:

(I) the fusion protein according to the first aspect of the present invention; and (II) a pharmaceutically acceptable carrier.

In another preferred embodiment, the pharmaceutical composition is used to prepare a drug for the prevention and/or treatment of a metabolic disease associated with diabetes or obesity, wherein the metabolic disease associated with diabetes or obesity includes: type I diabetes, type II diabetes, gestational diabetes, adiposis, non-alcoholic steatohepatitis (NASH), and non-alcoholic fatty liver disease (NAFLD).

In another preferred embodiment, the pharmaceutical composition further comprises other medicaments that can be used to prevent and/or treat a metabolic disease associated with diabetes or obesity.

In the seventh aspect of the present invention, it provides a use of the fusion protein according to the first aspect of the present invention or the pharmaceutical composition according to the sixth aspect of the present invention in the manufacture of a medicament for:

(i) controlling the blood glucose content in the body of a subject in need thereof;

(ii) reducing the blood lipid content in the body of a subject in need thereof;

(iii) reducing the body fat rate, or suppressing weight gain of a subject in need thereof;

(iv) improving liver function; and/or (v) preventing and/or treating a metabolic disease associated with diabetes or obesity.

In another preferred embodiment, the blood lipid comprises total cholesterol and low-density lipoprotein cholesterol.

In another preferred embodiment, the medicament is used for reducing the body fat rate, or suppressing weight gain of a subject in need thereof.

In another preferred embodiment, the metabolic disease associated with diabetes or obesity includes: type I diabetes, type II diabetes, gestational diabetes, obesity, non-alcoholic steatohepatitis (NASH), and non-alcoholic fatty liver disease (NAFLD).

In the eighth aspect of the present invention, it provides a method for preventing and/or treating a metabolic disease associated with diabetes or obesity, which comprises a step of administering an effective amount of the fusion protein according to the first aspect of the present invention, or the pharmaceutical composition according to the sixth aspect of the present invention, to a subject in need thereof.

It should be understood that within the scope of the present invention, the above-mentioned technical features of the present invention and the technical features specifically described in the following (such as the Examples) can be combined with each other to form a new or preferred technical solution, which are not redundantly repeated one by one due to space limitation.

EMBODIMENTS

Figure 1:
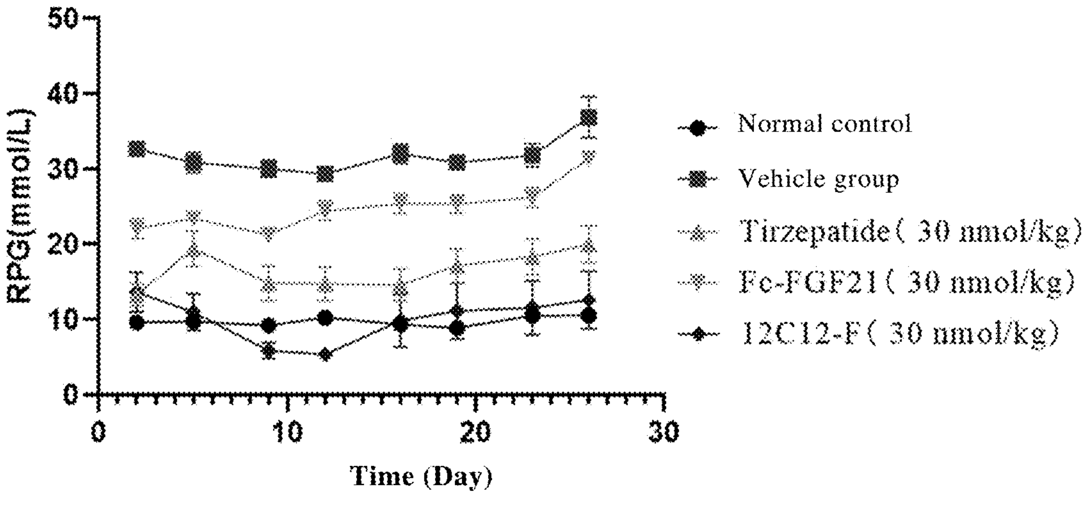
FIG. 1 shows random blood glucose in db/db diabetic mice after multiple dosing.

After extensive and intensive research and massive screening, the inventors have developed a fusion protein with triple activities of GLP-1, GIP and FGF21 for the first time. The fusion protein obtained can significantly reduce the body weight, plasma total cholesterol and low-density lipoprotein cholesterol of DIO mice, improve liver function and reduce the blood glucose of db/db mice. Its effect is significantly superior to that of single GLP-1/GIP active protein or FGF21 active protein. On this basis, the inventors have completed the present invention.

Terms

Unless specifically indicated otherwise, all technical and scientific terms used herein have the same meaning as commonly understood by those of ordinary skill in the art to which this invention belongs.

The term "about" may refer to a value or composition within an acceptable error range of a particular value or composition determined by a person of ordinary skill in the art, which will depend in part on how the value or composition is measured or determined.

As used herein, the term "containing" or "comprising (including)" can be open, semi-closed, and closed. In other words, the term also includes "substantially consisting of" or "consisting of".

Glucagon-Like Peptide-1 (GLP-1)

Glucagon-like peptide 1 (GLP-1) is a 37-amino acid incretin that stimulates insulin secretion, protects pancreatic beta cells, and inhibits glucagon secretion, gastric emptying and food intake, leading to weight loss. Liraglutide and Semaglutide are GLP-1 receptor agonists that are approved for the treatment of type 2 diabetes and obesity. However, many patients with type 2 diabetes and obesity remain inadequately controlled. Currently, commercially available incretin mimetics or dipeptidyl peptidase IV (DPP-IV) inhibitors use only a single established mechanism for blood glucose and weight control.

Glucose-Dependent Insulinotropic Polypeptide (GIP)

Glucose-dependent insulinotropic polypeptide (GIP) is a 42-amino acid gastrointestinal regulatory peptide, which plays a physiological role in glucose homeostasis by stimulating insulin secretion from pancreatic B cells and protecting pancreatic B cells in the presence of glucose. In the prior art, LY3298176, a GLP-1/GIP receptor dual agonist compound based on the natural GIP polypeptide sequence, is described as having favorable effects in reducing blood glucose and body weight and is currently approved by FDA for the treatment of type 2 diabetes, with the generic name Tirzepatide.

Fibroblast Growth Factor 21 (FGF21)

Fibroblast growth factor 21 (FGF21) is a member of fibroblast growth factors (FGFs) family with 182 amino acids. FGF21 can promote the absorption of glucose by adipocytes, enhance insulin sensitivity, and does not pose a potential tumor risk due to its lack of mitogenic activity. In addition, FGF21 also has a good lipid-lowering effect by inhibiting liver SREBP-2 synthesis, reducing serum total cholesterol and low-density lipoprotein content, thereby alleviating hypercholesterolemia. However, natural FGF21 also has some drawbacks, such as a tendency to aggregate in vitro, poor stability, a tendency to be hydrolyzed by protease, and a short half-life in vivo with a half-life of only 2-3 hours in cynomolgus macaques. These drawbacks limit the application of FGF21. Therefore, there are multiple methods to improve FGF21, such as mutating the arginine (R) at position 19 into valine (V), adding N-glycosylation sites and connecting IgG Fc to the C-terminus, which can inhibit the degradation of FGF21 in vitro and prolong its half-life in cynomolgus macaques. The half-life of FGF21 in cynomolgus macaques is increased to about 70 hours through the L98R, P171G, and A180E mutations.

Fusion Protein of the Present Invention

In the present invention, it provides a fusion protein having a triple bioactivity of glucagon-like peptide-1 (GLP-1), glucose-dependent insulinotropic polypeptide (GIP), and epidermal growth factor 21 (FGF21).

As used herein, the terms "the fusion protein of the present invention", "the triple bioactive fusion protein of the present invention", and "the fusion protein with triple activity" are used interchangeably. The fusion protein has a structure as shown in formula I or formula II from N-terminus to C-terminus,

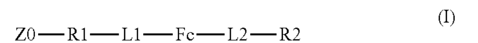

(I)

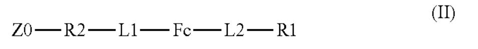

(II)

wherein,

Z0 is absent, or selected from: a signal peptide, a tag sequence, or a combination thereof;

R1 is a mutant protein element of GLP-1 and GIP;

L1 is absent or a linker peptide;

Fc is an Fc element;

L2 is absent or a linker peptide;

R2 is a FGF21 element;

"-" is a bond, wherein, the mutant protein element of GLP-1 and GIP comprises a GLP-1 and GIP mutant protein, wherein the amino acid sequence of the mutant protein is a polypeptide sequence based on the amino acid sequence shown in SEQ ID NO: 20 with amino acid residues at positions 1, 2, 13, 19, 21, 23, 24 selected from the group consisting of:

His or Tyr at position 1,

Gly or Ser at position 2,

Tyr or Leu at position 13,

Ala or Gln at position 19,

Ala or Asp at position 21,

Val or Ile at position 23, and

Ala or Gln or Glu at position 24; and wherein the mutant protein has the activity of binding and activating both a class B G protein-coupled receptor GLP-1R and a human glucose-dependent insulinotropic polypeptide (GIP) receptor.

As used herein, the terms "GLP-1 and GIP mutant protein", "GLP-1 and GIP mutant", and "GLP-1 and GIP mutant polypeptide" are used interchangeably and refer to the GLP-1 and GIP mutant protein of the present invention that has the activity of binding and activating both a class B G protein-coupled receptor GLP-1R and a human glucose-dependent insulinotropic polypeptide (GIP) receptor.

As used herein, the "linker" is preferably a flexible linker, usually a linking peptide that may be rich in G, S, and/or A, for example, may consist of glycine G, serine S, and alanine A, and a preferred linker is $(G4S)_nA$ or a variant thereof, wherein n is a positive integer (for example, 1, 2, 3, 4, 5 or 6), preferably, n=3; the variant of $(G4S)_nA$ comprises: a variant of the $(G4S)_nA$ linker sequence obtained by substituting amino acids in the sequence with those having similar or close properties, for example, mutating one or more S into T; or inserting 1-3 amino acids into the sequence.

In another preferred embodiment, the L1s are each independently $(G4S)_nA$, and n is a positive integer selected from 2 to 5 (for example, 1, 2, 3, 4, 5, or 6), preferably n is 3.

In another preferred embodiment, the L2s are each independently (G4S) n, and n is a positive integer selected from 2 to 5 (for example, 1, 2, 3, 4, 5, or 6), preferably n is 3.

Preferably, in the fusion protein of the present invention, the sequence of $R^1$ is selected from any of the amino acid sequences shown in SEQ ID NOs. 8-19, the sequence of R2 is selected from the amino acid sequences shown in SEQ ID NO. 1 or 2 (preferably the FGF21 mutant sequence shown in SEQ ID NO. 2), and the sequence of Fc is selected from the amino acid sequence shown in SEQ ID NO. 21; the sequence of L1 is shown in SEQ ID NO. 22, and the sequence of L2 is shown in SEQ ID NO. 23.

More preferably, the fusion protein of the present invention has the amino acid sequence shown in SEQ ID NOs: 4-7.

As used herein, the term "fusion protein of the present invention" also includes variant forms with the above-mentioned activities. These variant forms include (but are not limited to): deletion, insertion and/or substitution of 1-3 (usually 1-2, more preferably 1) amino acids, and addition or deletion of one or several (usually within 3, preferably within 2, more preferably within 1) amino acids at the C-terminus and/or N-terminus. For example, in this art, substitution with amino acids with similar or close properties usually does not alter the function of a protein. For another example, addition or deletion of one or several amino acids at the C-terminus and/or N-terminus usually also does not alter the structure and function of a protein. In addition, the term also includes the polypeptides of the present invention in monomeric and multimeric forms. The term also includes linear and non-linear polypeptides (such as cyclic peptides).

Active fragments, derivatives and analogs of the above-mentioned fusion protein are also included in the present invention. As used herein, the terms "fragment", "derivative" and "analog" refer to a polypeptide that substantially retains the function or activity of the GLP-1 and GIP mutant protein or fusion protein of the present invention. The polypeptide fragment, derivative or analog of the present invention can be (i) a polypeptide with substitution of one or several conservative or non-conservative amino acid residues (preferably conservative amino acid residues), or (ii) a polypeptide with a substitution group in one or more amino acid residues, or (iii) a polypeptide formed by fusion of the polypeptide with another compound (such as a compound that extends the half-life of the polypeptide, such as polyethylene glycol), or (iv) a polypeptide formed by fusion of an additional amino acid sequence with this polypeptide sequence (a fusion protein formed by fusion with a leader sequence, a secretion sequence, or a tag sequence such as 6His). According to the teachings herein, these fragments, derivatives and analogs belong to the scope well known to those skilled in the art.

A preferred type of the active derivative refers to a polypeptide formed by substitution of at most 3, preferably at most 2, and more preferably at most 1 amino acids with an amino acid having similar or close properties, compared with the amino acid sequence of the present invention. These conservative variant polypeptides are preferably produced by the amino acid substitution according to Table A.

TABLE A

| Initial Residue | Representative Substitution | Preferred Substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Analogs of the fusion protein of the present invention are also provided in the present invention. The difference between these analogs and the polypeptide of the present invention may be the difference in amino acid sequences, the difference in modification form that does not affect the sequence, or both. The analog also includes an analog with residues different from natural L-amino acids (such as D-amino acids), and an analog with non-naturally occurring or synthetic amino acids (such as β, γ-amino acids). It should be understood that the polypeptide of the present invention is not limited to the representative polypeptide exemplified above.

In addition, the fusion protein of the present invention can also be modified. Modification (usually without altering the primary structure) forms include: a chemically derived form of a polypeptide in vivo or in vitro, such as acetylation or carboxylation. The modification also includes glycosylation, such as those polypeptides produced by glycosylation modification during the synthesis and processing of the polypeptide or during further processing steps. This modification can be accomplished by exposing the polypeptide to an enzyme for glycosylation (such as a mammalian glycosylase or deglycosylase). Modification forms also include a sequence with phosphorylated amino acid residues (e.g., phosphotyrosine, phosphoserine, phosphothreonine). A polypeptide that has been modified thereby improving its resistance to proteolysis or optimizing its solubility, is also included.

The term "polynucleotide of the present invention" may include a polynucleotide encoding the GLP-1 and GIP mutant protein or fusion protein of the present invention, or may also include a polynucleotide of an additional encoding and/or non-encoding sequence.

A variant of the aforementioned polynucleotide, which encodes a fragment, analog and derivative of the polypeptide or fusion protein with the same amino acid sequence as the present invention, is also related to the present invention. These nucleotide variants include substitution variants, deletion variants and insertion variants. As known in the art, an allelic variant is an alternative form of a polynucleotide, which may be a substitution, deletion or insertion of one or more nucleotides, but will not substantially alter the function of the GLP-1 and GIP mutant protein or fusion protein it encodes. A polynucleotide that hybridizes with the aforementioned sequence and has at least 50%, preferably at least 70%, and more preferably at least 80% identity between the two sequences, is also related to the present invention. A polynucleotide that can hybridize with the polynucleotide of the present invention under strict conditions (or stringent conditions) is particularly related to the present invention. In the present invention, "strict conditions" refer to: (1) hybridization and elution at lower ionic strength and higher temperature, such as 0.2×SSC, 0.1% SDS, 60° C.; or (2) a denaturant is added during hybridization, such as 50% (v/v) formamide, 0.1% calf serum/0.1% Ficoll, 42° C., etc.; or (3) the hybridization occurs only when the identity between two sequences is at least more than 90%, preferably more than 95%.

The fusion protein and polynucleotide of the present invention are preferably provided in an isolated form, and more preferably, are purified to homogeneity.

The full-length sequence of the polynucleotide of the present invention can usually be obtained by PCR amplification method, recombination method or artificial synthesis method. For the PCR amplification method, primers can be designed according to the relevant nucleotide sequence disclosed in the present invention, especially the open reading frame sequence, and a commercially available cDNA library or a cDNA library prepared by a conventional method known to those skilled in the art can be used as a template to amplify the relevant sequence. When the sequence is long, two or more PCR amplifications are often necessary to be performed, and then the amplified fragments are spliced together in the correct order.

Once the relevant sequence is obtained, the recombination method can be used to obtain the relevant sequence in large quantities. This method is usually done by cloning the relevant sequence into a vector, then transferring the vector into a cell, and then isolating and obtaining the relevant sequence from the proliferated host cell by conventional methods.

In addition, the artificial synthesis method can also be used to synthesize the related sequence, especially when the fragment length is short. Typically, a fragment with a very long sequence can be obtained by first synthesizing multiple small fragments, and then ligating them.

At present, a DNA sequence encoding the protein (or fragment or derivative thereof) of the present invention can be obtained completely through chemical synthesis. The DNA sequence can then be introduced into various existing DNA molecules (or such as vectors) and cells known in the art.

The method of using PCR technology to amplify DNA/RNA is preferably used to obtain the polynucleotide of the present invention. Especially when it is difficult to obtain full-length cDNA from the library, the RACE method (RACE-rapid amplification of cDNA ends method) can be preferably used. The primers used for PCR can be appropriately selected according to the sequence information of the present invention disclosed herein, and can be synthesized by conventional methods. The amplified DNA/RNA fragments can be separated and purified by conventional methods such as gel electrophoresis.

Expression Vector

A vector comprising the polynucleotide of the present invention, and a host cell produced by genetic engineering using the vector of the present invention or an encoding sequence of the fusion protein of the present invention, and a method for producing the polypeptide of the present invention through recombinant technology, are also related to the present invention.

Through conventional recombinant DNA technology, the polynucleotide sequence of the present invention can be used to express or produce a recombinant fusion protein. Generally, the following steps are included:

(1) transforming or transducing a suitable host cell by using the polynucleotide (or variant) of the present invention encoding the fusion protein of the present invention, or using a recombinant expression vector comprising the polynucleotide;

(2) culturing the host cell in a suitable medium;

(3) separating and purifying the protein from the culture medium or cells.

In the present invention, the polynucleotide sequence encoding the fusion protein can be inserted into the recombinant expression vector. The term "recombinant expression vector" refers to bacterial plasmids, bacteriophages, yeast plasmids, plant cell viruses, and mammalian cell viruses such as adenovirus, retrovirus or other vectors well known in the art. Any plasmid and vector can be used as long as it can be replicated and stabilized in the host. An important feature of an expression vector is that it usually comprises an origin of replication, a promoter, a marker gene, and a translation control element.

Methods well known to those skilled in the art can be used to construct an expression vector comprising a DNA encoding sequence of the fusion protein of the present invention and an appropriate transcription/translation control signal. These methods include in vitro recombinant DNA technology, DNA synthesis technology, and in vivo recombination technology, etc. The DNA sequence can be effectively linked to an appropriate promoter in the expression vector to guide mRNA synthesis. Representative examples of these promoters are: lac or trp promoter of *Escherichia coli*; A phage PL promoter; eukaryotic promoters including CMV immediate early promoter, HSV thymidine kinase promoter, early and late SV40 promoter, LTRs of retroviruses and some other known promoters which can control the gene expression in prokaryotic or eukaryotic cells or viruses. The expression vector also includes a ribosome binding site for translation initiation and a transcription terminator.

In addition, the expression vector preferably comprises one or more selectable marker genes to provide phenotypic traits for selection of transformed host cells, such as dihydrofolate reductase, neomycin resistance, and green fluorescent protein (GFP) for eukaryotic cell culture, or tetracycline or ampicillin resistance for *Escherichia coli*.

A vector comprising the above-mentioned appropriate DNA sequence and an appropriate promoter or control sequence can be used to transform an appropriate host cell so that it can express a protein.

The host cell can be a prokaryotic cell, such as a bacterial cell; or a lower eukaryotic cell, such as a yeast cell; or a higher eukaryotic cell, such as a mammalian cell. Representative examples include: *Escherichia coli, Streptomyces*; bacterial cells of *Salmonella typhimurium*; fungal cells such as yeast and plant cells (such as *ginseng* cells).

When the polynucleotide of the present invention is expressed in higher eukaryotic cells, if an enhancer sequence is inserted into the vector, the transcription will be enhanced. Enhancers are cis-acting factors of DNA, usually with about 10 to 300 base pairs, acting on promoters to enhance gene transcription. Examples that can be enumerated include the SV40 enhancer with 100 to 270 base pairs on the late side of the replication origin, the polyoma enhancer on the late side of the replication origin, and the adenovirus enhancer, etc.

Those of ordinary skill in the art know how to select appropriate vectors, promoters, enhancers and host cells.

Transformation of a host cell with a recombinant DNA can be carried out by conventional techniques well known to those skilled in the art. When the host is a prokaryotic organism such as *Escherichia coli*, competent cells that can absorb DNA can be harvested after the exponential growth phase then treated with the $CaCl_2$) method, and the steps used are well known in the art. Another method is to use $MgCl_2$. If necessary, the transformation can also be carried out by electroporation. When the host is a eukaryote, the following DNA transfection methods can be selected: calcium phosphate co-precipitation method, conventional mechanical methods such as microinjection, electroporation, liposome packaging, etc.

The obtained transformants can be cultured by conventional methods to express the polypeptide encoded by the gene of the present invention. Depending on the host cell used, the medium used during the culture can be selected from various conventional mediums. The culture is carried out under conditions suitable for the growth of the host cell. When the host cell has grown to an appropriate cell density, a suitable method (such as temperature conversion or chemical induction) is used to induce the selected promoter, and the cell is cultured for another period of time.

The recombinant polypeptide of the above method can be expressed in the cell or on the cell membrane, or secreted out of the cell. If necessary, the physical, chemical, and other characteristics can be used to separate and purify the recombinant protein through various separation methods. These methods are well known to those skilled in the art. Examples of these methods include, but are not limited to: conventional renaturation treatment, treatment with protein precipitation agent (salting out method), centrifugation, osmotic shock method, ultra-treatment, ultra-centrifugation, molecular sieve chromatography (gel filtration), adsorption chromatography, ion exchange chromatography, high performance liquid chromatography (HPLC) and various other liquid chromatography techniques and combinations of these methods.

Main advantages of the present invention include:

(1) The present invention provides a novel GLP-1/GIP/FGF21 triple activity fusion protein for the first time, which has more advantages over the existing single or dual activity proteins in controlling blood glucose, body weight and blood lipids.

(2) The fusion protein of the present invention can significantly reduce the body weight, body fat ratio, plasma total cholesterol and low-density lipoprotein cholesterol of mice, improve liver function and lower mouse blood glucose. Its effects are significantly better than the single GLP-1/GIP active protein or FGF21 active protein, and it has a synergistic effect.

(3) The fusion protein of the present invention can be used to treat type 2 diabetes (T2D), obesity and other diseases with abnormal glucose and lipid metabolic abnormalities.

The present invention will be further illustrated below with reference to the specific examples. It should be understood that these examples are only to illustrate the invention, not to limit the scope of the invention. The experimental methods with no specific conditions described in the following examples are generally performed under the conventional conditions (e.g., the conditions described by Sambrook et al., Molecular Cloning: A Laboratory Manual (New York: Cold Spring Harbor Laboratory Press, 1989), or according to the manufacturer's instructions. Unless indicated otherwise, all percentage and parts are calculated by weight.

The structure of the fusion protein of the present invention is shown in the following formula:

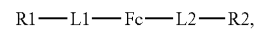

wherein, R1 is a polypeptide with dual activity of GLP-1 and GIP, L1 and L2 are linkers, Fc is an IgG Fc fragment, and R2 is FGF21 or a mutant thereof.

R1 has a sequence of the following structure with dual activity of GLP-1 and GIP:

(SEQ ID NO. 20)
$X_1X_2$EGTFTSDYSI$X_{13}$LDKIA$X_{19}$K$X_{21}$F$X_{23}X_{24}$WLIAGGPSSGAPPS wherein, $X_1$ is His or Tyr,
$X_2$ is Gly or Ser,
$X_{13}$ is Tyr or Leu,
$X_{19}$ is Ala or Gln,
$X_{21}$ is Ala or Asp,
$X_{23}$ is Val or Ile,
$X_{24}$ is Ala or Gln or Glu,
L1 and/or L2 are linkers;
Fc is an IgG Fc fragment, which can be selected from IgG1, IgG2 and IgG4, and whose main function is to prolong the half-life;
R2 is FGF21 or a mutant thereof, preferably an FGF21 mutant, wherein the amino acid sequence of the FGF21 mutant is a peptide sequence based on the amino acid sequence shown in SEQ ID NO.1 with amino acid residues at positions 19, 98, 171 and/or 173 selected from the group consisting of R19V, L98R, P171N, and Q173T.
Wherein, L1 is (G4S) 3A, and L2 is (G4S) 3.

Example 1: Preparation of Fusion Protein Samples

The corresponding genes were chemically synthesized according to the amino acid sequence of 12C1-F, 12C2-F, 12C3-F, 12C4-F, 12C5-F, 12C6-F, 12C7-F, 12C8-F, 12C9-F, 12C10-F, 12C11-F, and 12C12-F fusion proteins, and cloned into the pcDNA3.1 vector. A large amount of plasmids were extracted and transfected into ExpiCHO-S cells (Life Technologies). Feed and Enhancer were added after 24 hours of transfection, and the cells were cultured in a constant temperature shaking table under conditions of 5%, 120 rpm, and 32° C. After culturing for 7 days, the cell liquid was centrifuged (10000×g) for 30 min, and the supernatant obtained after centrifugation was filtered with a 0.45 μm filter. The filtrate was loaded onto a MabSelect SuRe column equilibrated with phosphate buffer. The column was then washed with 10 column volumes of phosphate buffer. The bound fusion protein was eluted with 50 mmol/L citrate acid buffer (pH3.0), and then neutralized to pH 7.0 with 1 mol/L Tris-HCl solution. The purity of the fusion protein was detected by HPLC-SEC. The absorbance value of the fusion protein at 280 nm was measured by an ultraviolet spectrophotometer, and the content of the fusion protein was calculated according to the extinction coefficient and purity of the fusion protein.

Example 2: Determination of In Vitro Biological Activity of Fusion Proteins

CHO-K1 cells expressing human GLP-1 receptor and CRE-luciferase were used to detect the in vitro GLP-1 activity of the fusion proteins. The cells were inoculated in a 96-well plate at a density of 30,000 cells/well/100 μL, and cultured at 5% $CO_2$, 37° C. for 1 hour. For each protein sample to be tested, the protein solution was diluted 9 times with a 4-fold gradient with PBS containing 2% HAS starting from a certain concentration, so that 10 dilutions of each sample with different concentrations were obtained. 50 μL of each dilution was taken out and added into the 96-well plate inoculated with cells, and the 96-well plate was incubated at 5% $CO_2$, 37° C. for 5 hours. The 96-well plate was taken out from the incubator and placed at room temperature for 10 minutes of equilibration, and 100 μL of reaction solution was added into each well. After the 96-well plate was shaken at 200 rpm for 10 minutes, the fluorescence reading of each well was detected by a multi-function microplate reader. Using the sample concentration as the abscissa and the fluorescence reading as the ordinate, a curve was drawn and the median effective concentration (EC50) of each sample was calculated. Tirzepatide was used as a positive control, and the results are shown in the table below.

CHO-K1 cells expressing human GIP receptor and CRE-luciferase were used to detect the in vitro GIP activity of the fusion proteins. The cells were inoculated in a 96-well plate at a density of 30,000 cells/well/100 μL, and cultured at 5% $CO_2$, 37° C. for 1 hour. For each protein sample to be tested, the protein solution was diluted 9 times with a 4-fold gradient with PBS containing 2% HAS starting from a certain concentration, so that 10 dilutions of each sample with different concentrations were obtained. 50 μL of each dilution was taken out and added into the 96-well plate inoculated with cells, and the 96-well plate was incubated at 5% $CO_2$, 37° C. for 5 hours. The 96-well plate was taken out from the incubator and placed at room temperature for 10 minutes of equilibration, and 100 μL of reaction solution was added into each well. After the 96-well plate was shaken at 200 rpm for 10 minutes, the fluorescence reading of each well was detected by a multi-function microplate reader. Using the sample concentration as the abscissa and the fluorescence reading as the ordinate, a curve was drawn and the median effective concentration (EC50) of each sample was calculated. Tirzepatide was used as a positive control, and the results are shown in the table below. The activity of some of the selected fusion proteins is much higher than that of the control Tirzepatide.

TABLE 1

Bioactivity of fusion proteins in vitro

| Sample | GLP-1 EC50 (nmol/L) | GIP EC50 (nmol/L) |
|---|---|---|
| Tirzepatide | 12.814 | 0.059 |
| Fc-FGF21 mutant | — | — |
| 12C1-F | 0.830 | 0.064 |
| 12C2-F | 2.659 | 0.073 |
| 12C3-F | 0.515 | 0.055 |
| 12C4-F | 2.563 | 0.056 |
| 12C5-F | 6.321 | 0.032 |
| 12C6-F | 7.125 | 0.009 |
| 12C7-F | 0.988 | 0.093 |
| 12C8-F | 2.235 | 0.022 |
| 12C9-F | 10.693 | 0.093 |
| 12C10-F | 7.355 | 0.111 |
| 12C11-F | 0.255 | 0.036 |
| 12C12-F | 0.642 | 0.006 |

Note:
The main difference between the different sequences is based on the mutations at different positions of R1

$X_1X_2$EGTFTSDYSI$X_{13}$LDKIA$X_{19}$K$X_{21}$F$X_{23}X_{24}$WLIAGGPSSGAPPPS

The results show that 12C1-F, 12C3-F, 12C11-F and 12C12-F are the preferred fusion proteins based on the in vitro activities of GLP-1 and GIP. The 12C12-F fusion protein with the best comprehensive performance was selected for subsequent experiments.

Example 3: Experiments on Reducing Blood Glucose by Multiple Subcutaneous Injections in db/db Diabetes Mice The purpose of this example is to investigate the effects of subcutaneous injection of 12C12-F fusion protein on blood glucose and other indicators of db/db mice, and to compare its pharmacological effects with Tirzepatide and Fc-FGF21.

Figure 2:
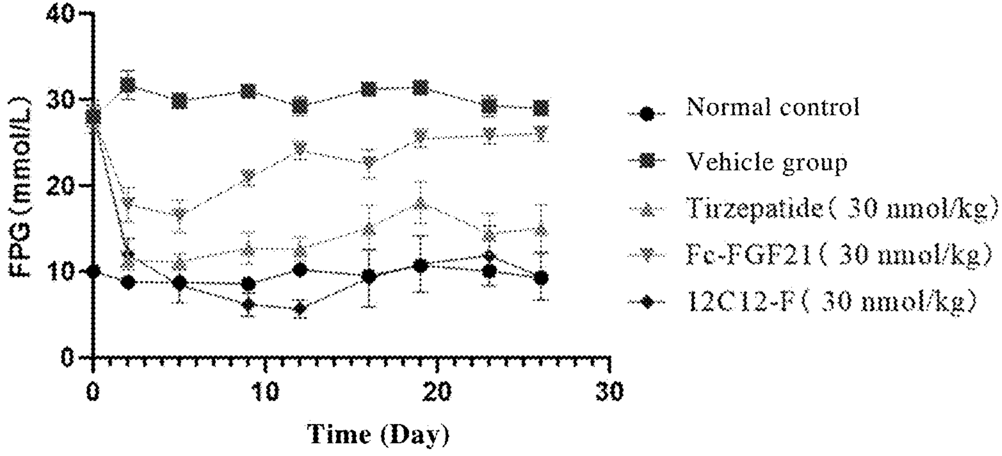
FIG. 2 shows fasting blood glucose in db/db diabetic mice after multiple dosing.

After adaptive feeding of animals, fasting blood glucose following a 4-hour fasting period was measured once a week. Except for the 6 mice in control group (Wild type), db/db mice were divided into groups for experiments after their 4-hour fasting blood glucose levels reached the high blood glucose standard (>16.7 mmol/L). Twenty-four male db/db mice that reached the high blood glucose standard were divided into 4 groups based on their blood glucose levels and body weight, with 6 mice in each group. Group design: Tirzepatide group, Fc-FGF21 group, 12C12-F group, vehicle group (PBS), and a normal mouse control group (Wild type) was set up at the same time. After the experimental animals were grouped, corresponding drug treatment was administered subcutaneously (twice a week) at a dose of 30 nmol/kg. During the administration period, random blood glucose and fasting blood glucose (fasting for 4 hours) were measured twice a week. Random blood glucose is shown in FIG. 1, and fasting blood glucose is shown in FIG. 2.

The results show that the hypoglycemic effect of 12C12-F is significantly better than that of Tirzepatide (GLP-1/GIP dual activity) and Fc-FGF21 (FGF21 single activity). The blood glucose level in 12C12-F group is basically identical to that of the normal control group, that is, the blood glucose of diabetic mice has returned to normal.

Example 4: Experiments on Body Weight Reduction by Administration of Multiple Subcutaneous Injections in DIO Mice The purpose of this example is to investigate the effects of subcutaneous injection of fusion protein on body weight and other indicators of DIO mice, and to compare its pharmacological effects with Tirzepatide.

7-week-old C57BL/6Nju mice were fed with a high-fat diet (of about 20% protein and about 60% fat) for 12 weeks for modeling. Feeding conditions: 12 hours of light and 12 hours of darkness cycle every day, ad libitum feeding, temperature 20-25° C., relative humidity 40-70%, ventilation frequency of 10-15 times/hour. According to body weight, water consumption, and food intake, the mice were randomly divided into groups the day before administration. Group design: Tirzepatide group, Fc-FGF21 group, 12C12-F group, vehicle group (PBS), and normal control group, with 6 mice in each group. Subcutaneous injection treatment was administered twice a week for 5 consecutive weeks, for a total of 10 administrations. After the administration, the body weight, OGTT, body fat ratio, blood lipids and liver function of the mice were measured. The data are shown as mean±standard deviation, and statistically analyzed by One-Way ANOVA.

12C12-F can significantly reduce the body weight and body fat ratio of DIO obese mice, and the reduction extent is significantly greater than that of the control Tirzepatide and Fc-FGF21. At the same time, it can significantly reduce blood glucose, plasma total cholesterol and low-density lipoprotein cholesterol, improve liver function, and basically return them to normal.

TABLE 2

Changes of body weight and body fat ratio in DIO obese mice after administration

| Sample | % Change in weight since inception | Body fat ratio(%) |
|---|---|---|
| Model control | 11.94 ± 4.03 | 47.98 ± 3.72 |
| Tirzepatide (30 nmol/kg) | −22.55 ± 4.05**** | 32.20 ± 3.87**** |
| Fc-FGF21 (30 nmol/kg) | −6.65 ± 3.33** | 42.88 ± 3.88 |
| 12C12-F (30 nmol/kg) | −39.73 ± 4.28 | 16.16 ± 5.56**** |

**p < 0.01,
****p < 0.0001
Compared with the control group (One-Way ANOVA, Dunnett's).
The results are expressed as mean ± SD for 6 mice in each group.

TABLE 3

Fasting blood glucose, liver enzymes, plasma total cholesterol, and plasma low-density lipoprotein cholesterol in DIO mice

| Sample | Blood glucose (mmol/L) | ALT (U/L) | AST (U/L) | TC (mmol/L) | LDL-C (mmol/L) |
|---|---|---|---|---|---|
| Normal control | 7.8 ± 0.88** | 38.350 ± 24.67*** | 50.967 ± 3.24* | 3.753 ± 0.19**** | 0.347 ± 0.03**** |
| Model control | 10.1 ± 1.19 | 99.133 ± 53.56 | 109.367 ± 78.38 | 6.577 ± 0.92 | 0.952 ± 0.29 |
| Tirzepatide (30 nmol/kg) | 7.2 ± 0.22*** | 19.000 ± 2.91**** | 54.683 ± 5.53* | 3.923 ± 0.28**** | 0.423 ± 0.06**** |
| Fc-FGF21 (30 nmol/kg) | 9.12± | 88.365 ± 5.36 | 77.658 ± 56.32 | 5.364 ± 0.99 | 0.656 ± 0.31** |
| 12C12-F (30 nmol/kg) | 5.2 ± 0.44*** | 14.683 ± 2.19**** | 55.183 ± 5.22* | 3.348 ± 0.30**** | 0.383 ± 0.02**** |

*p < 0.05,
**p < 0.01,
***p < 0.001,
****p < 0.0001
Compared with the control group (One-Way ANOVA, Dunnett's).
The results are expressed as mean ± SD for 6 mice in each group.

The sequences of the present invention are as follows:

TABLE 4

The amino acid sequences of 12C1-12C12

| SEQ | Number | Sequence |
|---|---|---|
| 8 | 12C1 | **YG**EGTFTSDYSI**L**LDKIA**Q**K**A**F**IE**WLIAGGPSSGAPPPS |
| 9 | 12C2 | **HS**EGTFTSDYSI**Y**LDKIA**Q**K**A**F**IE**WLIAGGPSSGAPPPS |
| 10 | 12C3 | **YG**EGTFTSDYSI**Y**LDKIA**Q**K**A**F**IE**WLIAGGPSSGAPPPS |
| 11 | 12C4 | **HS**EGTFTSDYSI**L**LDKIA**A**K**D**F**IE**WLIAGGPSSGAPPPS |
| 12 | 12C5 | **YG**EGTFTSDYSI**L**LDKIA**A**K**D**F**VQ**WLIAGGPSSGAPPPS |
| 13 | 12C6 | **HG**EGTFTSDYSI**L**LDKIA**Q**K**D**F**VQ**WLIAGGPSSGAPPPS |
| 14 | 12C7 | **HS**EGTFTSDYSI**Y**LDKIA**A**K**D**F**IE**WLIAGGPSSGAPPPS |
| 15 | 12C8 | **YG**EGTFTSDYSI**Y**LDKIA**A**K**A**F**VQ**WLIAGGPSSGAPPPS |
| 16 | 12C9 | **HS**EGTFTSDYSI**L**LDKIA**A**K**D**F**VQ**WLIAGGPSSGAPPPS |
| 17 | 12C10 | **YS**EGTFTSDYSI**Y**LDKIA**A**K**A**F**VQ**WLIAGGPSSGAPPPS |
| 18 | 12C11 | **HG**EGTFTSDYSI**Y**LDKIA**A**K**D**F**IE**WLIAGGPSSGAPPPS |
| 19 | 12C12 | **HS**EGTFTSDYSI**L**LDKIA**Q**K**A**F**IE**WLIAGGPSSGAPPPS |

(wild type FGF21)

SEQ.ID NO 1

HPIPDSSPLLQFGGQVRQRYLYTDDAQQTEAHLEIREDGTVGGAADQSPESLLQLKALK

PGVIQILGVKTSRFLCQRPDGALYGSLHFDPEACSFRELLLEDGYNVYQSEAHGLPLHLPGN

KSPHRDPAPRGPARFLPLPGLPPALPEPPGILAPQPPDVGSSDPLSMVGPSQGRSPSYAS (FGF21 mutant)

SEQ.ID NO 2

HPIPDSSPLLQFGGQVRQVYLYTDDAQQTEAHLEIREDGTVGGAADQSPESLLQLKAL

KPGVIQILGVKTSRFLCQRPDGALYGSLHFDPEACSFRERLLEDGYNVYQSEAHGLPLHLPG

NKSPHRDPAPRGPARFLPLPGLPPALPEPPGILAPQPPDVGSSDPLSMVGNSTGRSPSYAS (Fc-FGF21 mutant)

SEQ.ID NO 3

ESKYGPPCPPCPAPEAAGGPSVFLFPPKPKDTLMISRTPEVTCVVVDVSQEDPEVQFNW

YVDGVEVHNAKTKPREEQFNSTYRVVSVLTVLHQDWLNGKEYKCKVSNKGLPSSIEKTISK

AKGQPREPQVYTLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGGGGGSGGGGSGGG

GSHPIPDSSPLLQFGGQVRQVYLYTDDAQQTEAHLEIREDGTVGGAADQSPESLLQLKALKP

GVIQILGVKTSRFLCQRPDGALYGSLHFDPEACSFRERLLEDGYNVYQSEAHGLPLHLPGNK

SPHRDPAPRGPARFLPLPGLPPALPEPPGILAPQPPDVGSSDPLSMVGNSTGRSPSYAS*

(12C1-F fusion protein)

SEQ.ID NO 4

YGEGTFTSDYSILLDKIAOKAFIEWLIAGGPSSGAPPPSGGGGSGGGGSGGGGSAESKY

GPPCPPCPAPEAAGGPSVFLFPPKPKDTLMISRTPEVTCVVVDVSQEDPEVQFNWYVDGVEV

HNAKTKPREEQFNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTPPVLDSDGSFFLY

SRLTVDKSRWQEGNVFSCSVMHEALHNHYTQKSLSLSLGGGGGSGGGGSGGGGSHPIPDSS

-continued

PLLQFGGQVRQVYLYTDDAQQTEAHLEIREDGTVGGAADQSPESLLQLKALKPGVIQILGV

KTSRFLCQRPDGALYGSLHFDPEACSFRERLLEDGYNVYQSEAHGLPLHLPGNKSPHRDPAP

RGPARFLPLPGLPPALPEPPGILAPQPPDVGSSDPLSMVGNSTGRSPSYAS (12C3-F fusion protein)

SEQ.ID NO 5

YGEGTFTSDYSIYLDKIAQKAFIEWLIAGGPSSGAPPPSGGGGSGGGGSGGGGSAESKY

GPPCPPCPAPEAAGGPSVFLFPPKPKDTLMISRTPEVTCVVVDVSQEDPEVQFNWYVDGVEV

HNAKTKPREEQFNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTPPVLDSDGSFFLY

SRLTVDKSRWQEGNVFSCSVMHEALHNHYTQKSLSLSLGGGGGSGGGGSGGGGSHPIPDSS

PLLQFGGQVRQVYLYTDDAQQTEAHLEIREDGTVGGAADQSPESLLQLKALKPGVIQILGV

KTSRFLCQRPDGALYGSLHFDPEACSFRERLLEDGYNVYQSEAHGLPLHLPGNKSPHRDPAP

RGPARFLPLPGLPPALPEPPGILAPQPPDVGSSDPLSMVGNSTGRSPSYAS (12C11-F fusion protein)

SEQ.ID NO 6

HGEGTFTSDYSIYLDKIAAKDFIEWLIAGGPSSGAPPPSGGGGSGGGGSGGGGSAESKY

GPPCPPCPAPEAAGGPSVFLFPPKPKDTLMISRTPEVTCVVVDVSQEDPEVQFNWYVDGVEV

HNAKTKPREEQFNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTPPVLDSDGSFFLY

SRLTVDKSRWQEGNVFSCSVMHEALHNHYTQKSLSLSLGGGGGSGGGGSGGGGSHPIPDSS

PLLQFGGQVRQVYLYTDDAQQTEAHLEIREDGTVGGAADQSPESLLQLKALKPGVIQILGV

KTSRFLCQRPDGALYGSLHFDPEACSFRERLLEDGYNVYQSEAHGLPLHLPGNKSPHRDPAP

RGPARFLPLPGLPPALPEPPGILAPQPPDVGSSDPLSMVGNSTGRSPSYAS (12C12-F fusion protein)

SEQ.ID NO 7

HSEGTFTSDYSILLDKIAQKAFIEWLIAGGPSSGAPPPSGGGGSGGGGSGGGGSAESKYG

PPCPPCPAPEAAGGPSVFLFPPKPKDTLMISRTPEVTCVVVDVSQEDPEVQFNWYVDGVEVH

NAKTKPREEQFNSTYRVVSVLTVLHQDWLNGKEYKCKVSNKGLPSSIEKTISKAKGQPREP

QVYTLPPSQEEMTKNQVSLTCLVKGFYPSDIAVEWESNGQPENNYKTTPPVLDSDGSFFLYS

RLTVDKSRWQEGNVFSCSVMHEALHNHYTQKSLSLSLGGGGGSGGGGSGGGGSHPIPDSSP

LLQFGGQVRQVYLYTDDAQQTEAHLEIREDGTVGGAADQSPESLLQLKALKPGVIQILGVK

TSRFLCQRPDGALYGSLHFDPEACSFRERLLEDGYNVYQSEAHGLPLHLPGNKSPHRDPAPR

GPARFLPLPGLPPALPEPPGILAPQPPDVGSSDPLSMVGNSTGRSPSYAS (Peptide template)

SEQ ID NO. 20

$X_1X_2$EGTFTSDYSI$X_{13}$LDKIA$X_{19}$K$X_{21}$F$X_{23}X_{24}$WLIAGGPSSGAPPPS

Wherein, $X_1$ is H or Y, $X_2$ is G or S, $X_{13}$ is Y or L, $X_{19}$ is A or Q, $X_{21}$ is A or D, $X_{23}$ is V or I, $X_{24}$ is A or Q or E (Fc fragment)

SEQ ID NO. 21

ESKYGPPCPPCPAPEAAGGPSVFLFPPKPKDTLMISRTPEVTCVVVDVSQEDPEVQF

NWYVDGVEVHNAKTKPREEQFNSTYRVVSVLTVLHQDWLNGKEYKCKVSNKGLPSSI

-continued

EKTISKAKGQPREPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKSLSLSLG (linker1)

SEQ ID NO. 22

GGGGSGGGGSGGGGSA (linker2)

SEQ ID NO. 23

GGGGSGGGGSGGGGS

All documents mentioned in the present invention are incorporated by reference herein as if each document was incorporated separately by reference. Furthermore, it should be understood that after reading the foregoing teachings of the present invention, various changes or modifications can be made to the present invention by those skilled in the art and that these equivalents also fall in the scope of the claims appended to this application.

The invention claimed is:

1. A polypeptide comprising the amino acid sequence of any one of SEQ ID NOS: 8, 10, 18, and 19.

2. The polypeptide of claim 1, comprising the amino acid sequence of SEQ ID NO: 8.

3. The polypeptide of claim 1, comprising the amino acid sequence of SEQ ID NO: 10.

4. The polypeptide of claim 1, comprising the amino acid sequence of SEQ ID NO: 18.

5. The polypeptide of claim 1, comprising the amino acid sequence of SEQ ID NO: 19.

6. The polypeptide of claim 1, further comprising an Fc region.

7. The polypeptide of claim 6, wherein the Fc region is an IgG4 Fc region.

8. The polypeptide of claim 6, wherein the Fc region comprises the amino acid sequence of SEQ ID NO: 21.

9. The polypeptide of claim 1, further comprising an FGF21 amino acid sequence.

10. The polypeptide of claim 9, wherein the FGF21 amino acid sequence is a mutant human FGF21 amino acid sequence comprising valine at position 19, arginine at position 98, asparagine at position 171, and/or threonine at position 173, wherein the amino acid position numbering is relative to the FGF21 amino acid sequence set forth in SEQ ID NO: 1.

11. The polypeptide of claim 9, wherein the FGF21 amino acid sequence comprises the amino acid sequence of SEQ ID NO: 2.

12. The polypeptide of claim 1, wherein the polypeptide comprises the amino acid sequence of any one of SEQ ID NOs: 4-7.

13. The polypeptide of claim 1, wherein the polypeptide comprises the amino acid sequence of SEQ ID NO: 4.

14. The polypeptide of claim 1, wherein the polypeptide comprises the amino acid sequence of SEQ ID NO: 5.

15. The polypeptide of claim 1, wherein the polypeptide comprises the amino acid sequence of SEQ ID NO: 6.

16. The polypeptide of claim 1, wherein the polypeptide comprises the amino acid sequence of SEQ ID NO: 7.

17. A polynucleotide encoding the polypeptide of claim 1.

18. A vector comprising the polynucleotide of claim 17.

19. A host cell comprising the polynucleotide of claim 17.

20. A method of producing a polypeptide, the method comprising culturing the host cell of claim 19 under conditions such that the polypeptide is produced.

21. A polypeptide comprising a mutant human FGF21 amino acid sequence comprising valine at position 19, arginine at position 98, asparagine at position 171, threonine at position 173, serine at position 167 and arginine at position 175, wherein the amino acid position numbering is relative to the FGF21 amino acid sequence set forth in SEQ ID NO: 1.

22. A polynucleotide encoding the polypeptide of claim 21.

23. A vector comprising the polynucleotide of claim 22.

24. A host cell comprising the polynucleotide of claim 22.

25. A method of producing a polypeptide, the method comprising culturing the host cell of claim 24 under conditions such that the polypeptide is produced.

26. A polypeptide comprising the amino acid sequence of SEQ ID NO: 2.

* * * * *

SEQUENCE LISTING

```
Sequence total quantity: 23
SEQ ID NO: 1            moltype = AA  length = 181
FEATURE                 Location/Qualifiers
source                  1..181
                        mol_type = protein
                        note = Wild type FGF21
                        organism = synthetic construct
SEQUENCE: 1
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
NKSPHRDPAP RGPARFLPLP GLPPALPEPP GILAPQPPDV GSSDPLSMVG PSQGRSPSYA  180
S                                                                  181

SEQ ID NO: 2            moltype = AA  length = 181
FEATURE                 Location/Qualifiers
source                  1..181
                        mol_type = protein
                        note = FGF21 mutant
                        organism = synthetic construct
SEQUENCE: 2
HPIPDSSPLL QFGGQVRQVY LYTDDAQQTE AHLEIREDGT VGGAADQSPE SLLQLKALKP  60
GVIQILGVKT SRFLCQRPDG ALYGSLHFDP EACSFRERLL EDGYNVYQSE AHGLPLHLPG  120
NKSPHRDPAP RGPARFLPLP GLPPALPEPP GILAPQPPDV GSSDPLSMVG NSTGRSPSYA  180
S                                                                  181

SEQ ID NO: 3            moltype = AA  length = 424
FEATURE                 Location/Qualifiers
source                  1..424
                        mol_type = protein
                        note = Fc-FGF21 mutant fusion protein
                        organism = synthetic construct
SEQUENCE: 3
ESKYGPPCPP CPAPEAAGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGGG GGSGGGGSGG  240
GGSHPIPDSS PLLQFGGQVR QVYLYTDDAQ QTEAHLEIRE DGTVGGAADQ SPESLLQLKA  300
LKPGVIQILG VKTSRFLCQR PDGALYGSLH FDPEACSFRE RLLEDGYNVY QSEAHGLPLH  360
LPGNKSPHRD PAPRGPARFL PLPGLPPALP EPPGILAPQP PDVGSSDPLS MVGNSTGRSP  420
SYAS                                                               424

SEQ ID NO: 4            moltype = AA  length = 479
FEATURE                 Location/Qualifiers
source                  1..479
                        mol_type = protein
                        note = 12C1-F fusion protein
                        organism = synthetic construct
SEQUENCE: 4
YGEGTFTSDY SILLDKIAQK AFIEWLIAGG PSSGAPPPSG GGGSGGGGSG GGGSAESKYG  60
PPCPPCPAPE AAGGPSVFLF PPKPKDTLMI SRTPEVTCVV VDVSQEDPEV QFNWYVDGVE  120
VHNAKTKPRE EQFNSTYRVV SVLTVLHQDW LNGKEYKCKV SNKGLPSSIE KTISKAKGQP  180
REPQVYTLPP SQEEMTKNQV SLTCLVKGFY PSDIAVEWES NGQPENNYKT TPPVLDSDGS  240
FFLYSRLTVD KSRWQEGNVF SCSVMHEALH NHYTQKSLSL SLGGGGGSGG GGSGGGGSHP  300
IPDSSPLLQF GGQVRQVYLY TDDAQQTEAH LEIREDGTVG GAADQSPESL LQLKALKPGV  360
IQILGVKTSR FLCQRPDGAL YGSLHFDPEA CSFRERLLED GYNVYQSEAH GLPLHLPGNK  420
SPHRDPAPRG PARFLPLPGL PPALPEPPGI LAPQPPDVGS SDPLSMVGNS TGRSPSYAS   479

SEQ ID NO: 5            moltype = AA  length = 479
```

-continued

```
FEATURE                 Location/Qualifiers
source                  1..479
                        mol_type = protein
                        note = 12C3-F fusion protein
                        organism = synthetic construct
SEQUENCE: 5
YGEGTFTSDY SIYLDKIAQK AFIEWLIAGG PSSGAPPPSG GGGSGGGGSG GGGSAESKYG  60
PPCPPCPAPE AAGGPSVFLF PPKPKDTLMI SRTPEVTCVV VDVSQEDPEV QFNWYVDGVE  120
VHNAKTKPRE EQFNSTYRVV SVLTVLHQDW LNGKEYKCKV SNKGLPSSIE KTISKAKGQP  180
REPQVYTLPP SQEEMTKNQV SLTCLVKGFY PSDIAVEWES NGQPENNYKT TPPVLDSDGS  240
FFLYSRLTVD KSRWQEGNVF SCSVMHEALH NHYTQKSLSL SLGGGGGSGG GGSGGGGSHP  300
IPDSSPLLQF GGQVRQVYLY TDDAQQTEAH LEIREDGTVG GAADQSPESL LQLKALKPGV  360
IQILGVKTSR FLCQRPDGAL YGSLHFDPEA CSFRERLLED GYNVYQSEAH GLPLHLPGNK  420
SPHRDPAPRG PARFLPLPGL PPALPEPPGI LAPQPPDVGS SDPLSMVGNS TGRSPSYAS   479

SEQ ID NO: 6            moltype = AA  length = 479
FEATURE                 Location/Qualifiers
source                  1..479
                        mol_type = protein
                        note = 12C11-F fusion protein
                        organism = synthetic construct
SEQUENCE: 6
HGEGTFTSDY SIYLDKIAAK DFIEWLIAGG PSSGAPPPSG GGGSGGGGSG GGGSAESKYG  60
PPCPPCPAPE AAGGPSVFLF PPKPKDTLMI SRTPEVTCVV VDVSQEDPEV QFNWYVDGVE  120
VHNAKTKPRE EQFNSTYRVV SVLTVLHQDW LNGKEYKCKV SNKGLPSSIE KTISKAKGQP  180
REPQVYTLPP SQEEMTKNQV SLTCLVKGFY PSDIAVEWES NGQPENNYKT TPPVLDSDGS  240
FFLYSRLTVD KSRWQEGNVF SCSVMHEALH NHYTQKSLSL SLGGGGGSGG GGSGGGGSHP  300
IPDSSPLLQF GGQVRQVYLY TDDAQQTEAH LEIREDGTVG GAADQSPESL LQLKALKPGV  360
IQILGVKTSR FLCQRPDGAL YGSLHFDPEA CSFRERLLED GYNVYQSEAH GLPLHLPGNK  420
SPHRDPAPRG PARFLPLPGL PPALPEPPGI LAPQPPDVGS SDPLSMVGNS TGRSPSYAS   479

SEQ ID NO: 7            moltype = AA  length = 479
FEATURE                 Location/Qualifiers
source                  1..479
                        mol_type = protein
                        note = 12C12-F fusion protein
                        organism = synthetic construct
SEQUENCE: 7
HSEGTFTSDY SILLDKIAQK AFIEWLIAGG PSSGAPPPSG GGGSGGGGSG GGGSAESKYG  60
PPCPPCPAPE AAGGPSVFLF PPKPKDTLMI SRTPEVTCVV VDVSQEDPEV QFNWYVDGVE  120
VHNAKTKPRE EQFNSTYRVV SVLTVLHQDW LNGKEYKCKV SNKGLPSSIE KTISKAKGQP  180
REPQVYTLPP SQEEMTKNQV SLTCLVKGFY PSDIAVEWES NGQPENNYKT TPPVLDSDGS  240
FFLYSRLTVD KSRWQEGNVF SCSVMHEALH NHYTQKSLSL SLGGGGGSGG GGSGGGGSHP  300
IPDSSPLLQF GGQVRQVYLY TDDAQQTEAH LEIREDGTVG GAADQSPESL LQLKALKPGV  360
IQILGVKTSR FLCQRPDGAL YGSLHFDPEA CSFRERLLED GYNVYQSEAH GLPLHLPGNK  420
SPHRDPAPRG PARFLPLPGL PPALPEPPGI LAPQPPDVGS SDPLSMVGNS TGRSPSYAS   479

SEQ ID NO: 8            moltype = AA  length = 39
FEATURE                 Location/Qualifiers
source                  1..39
                        mol_type = protein
                        note = 12C1
                        organism = synthetic construct
SEQUENCE: 8
YGEGTFTSDY SILLDKIAQK AFIEWLIAGG PSSGAPPPS                        39

SEQ ID NO: 9            moltype = AA  length = 39
FEATURE                 Location/Qualifiers
source                  1..39
                        mol_type = protein
                        note = 12C2
                        organism = synthetic construct
SEQUENCE: 9
HSEGTFTSDY SIYLDKIAQK AFIEWLIAGG PSSGAPPPS                        39

SEQ ID NO: 10           moltype = AA  length = 39
FEATURE                 Location/Qualifiers
source                  1..39
                        mol_type = protein
                        note = 12C3
                        organism = synthetic construct
SEQUENCE: 10
YGEGTFTSDY SIYLDKIAQK AFIEWLIAGG PSSGAPPPS                        39

SEQ ID NO: 11           moltype = AA  length = 39
FEATURE                 Location/Qualifiers
source                  1..39
                        mol_type = protein
                        note = 12C4
```

```
                        organism = synthetic construct
SEQUENCE: 11
HSEGTFTSDY SILLDKIAAK DFIEWLIAGG PSSGAPPPS                          39

SEQ ID NO: 12           moltype = AA  length = 39
FEATURE                 Location/Qualifiers
source                  1..39
                        mol_type = protein
                        note = 12C5
                        organism = synthetic construct
SEQUENCE: 12
YGEGTFTSDY SILLDKIAAK DFVQWLIAGG PSSGAPPPS                          39

SEQ ID NO: 13           moltype = AA  length = 39
FEATURE                 Location/Qualifiers
source                  1..39
                        mol_type = protein
                        note = 12C6
                        organism = synthetic construct
SEQUENCE: 13
HGEGTFTSDY SILLDKIAQK DFVQWLIAGG PSSGAPPPS                          39

SEQ ID NO: 14           moltype = AA  length = 39
FEATURE                 Location/Qualifiers
source                  1..39
                        mol_type = protein
                        note = 12C7
                        organism = synthetic construct
SEQUENCE: 14
HSEGTFTSDY SIYLDKIAAK DFIEWLIAGG PSSGAPPPS                          39

SEQ ID NO: 15           moltype = AA  length = 39
FEATURE                 Location/Qualifiers
source                  1..39
                        mol_type = protein
                        note = 12C8
                        organism = synthetic construct
SEQUENCE: 15
YGEGTFTSDY SIYLDKIAAK AFVQWLIAGG PSSGAPPPS                          39

SEQ ID NO: 16           moltype = AA  length = 39
FEATURE                 Location/Qualifiers
source                  1..39
                        mol_type = protein
                        note = 12C9
                        organism = synthetic construct
SEQUENCE: 16
HSEGTFTSDY SILLDKIAAK DFVQWLIAGG PSSGAPPPS                          39

SEQ ID NO: 17           moltype = AA  length = 39
FEATURE                 Location/Qualifiers
source                  1..39
                        mol_type = protein
                        note = 12C10
                        organism = synthetic construct
SEQUENCE: 17
YSEGTFTSDY SIYLDKIAAK AFVQWLIAGG PSSGAPPPS                          39

SEQ ID NO: 18           moltype = AA  length = 39
FEATURE                 Location/Qualifiers
source                  1..39
                        mol_type = protein
                        note = 12C11
                        organism = synthetic construct
SEQUENCE: 18
HGEGTFTSDY SIYLDKIAAK DFIEWLIAGG PSSGAPPPS                          39

SEQ ID NO: 19           moltype = AA  length = 39
FEATURE                 Location/Qualifiers
source                  1..39
                        mol_type = protein
                        note = 12C12
                        organism = synthetic construct
SEQUENCE: 19
HSEGTFTSDY SILLDKIAQK AFIEWLIAGG PSSGAPPPS                          39

SEQ ID NO: 20           moltype = AA  length = 39
FEATURE                 Location/Qualifiers
source                  1..39
```

-continued

```
                        mol_type = protein
                        note = Polypeptide design template
                        organism = synthetic construct
VAR_SEQ                 1
                        note = X =H or Y
VAR_SEQ                 2
                        note = X =G or S
VAR_SEQ                 13
                        note = X= Y or L
VAR_SEQ                 19
                        note = X= A or Q
VAR_SEQ                 21
                        note = X= A or D
VAR_SEQ                 23
                        note = X= V or I
VAR_SEQ                 24
                        note = X= A or Q or E
SEQUENCE: 20
XXEGTFTSDY SIXLDKIAXK XFXXWLIAGG PSSGAPPPS                        39

SEQ ID NO: 21           moltype = AA  length = 228
FEATURE                 Location/Qualifiers
source                  1..228
                        mol_type = protein
                        note = Fc
                        organism = synthetic construct
SEQUENCE: 21
ESKYGPPCPP CPAPEAAGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLG               228

SEQ ID NO: 22           moltype = AA  length = 16
FEATURE                 Location/Qualifiers
source                  1..16
                        mol_type = protein
                        note = linker1
                        organism = synthetic construct
SEQUENCE: 22
GGGGSGGGGS GGGGSA                                                 16

SEQ ID NO: 23           moltype = AA  length = 15
FEATURE                 Location/Qualifiers
source                  1..15
                        mol_type = protein
                        note = linker2
                        organism = synthetic construct
SEQUENCE: 23
GGGGSGGGGS GGGGS                                                  15
```